(12) United States Patent
Nozato et al.

(10) Patent No.: US 9,016,861 B2
(45) Date of Patent: Apr. 28, 2015

(54) ADAPTIVE OPTICS APPARATUS, ADAPTIVE OPTICS METHOD, AND IMAGING APPARATUS

(75) Inventors: Koji Nozato, Yokohama (JP); Kazuhide Miyata, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 154 days.

(21) Appl. No.: 12/945,590

(22) Filed: Nov. 12, 2010

(65) Prior Publication Data

US 2011/0116044 A1     May 19, 2011

(30) Foreign Application Priority Data

Nov. 17, 2009   (JP) ................. 2009-262386

(51) Int. Cl.
*A61B 3/14* (2006.01)
*A61B 3/00* (2006.01)
*A61B 3/10* (2006.01)

(52) U.S. Cl.
CPC ....................... *A61B 3/14* (2013.01)

(58) Field of Classification Search
USPC .......... 351/206, 200, 203, 205, 210–211, 221
See application file for complete search history.

(56) References Cited

U.S. PATENT DOCUMENTS

| | | | |
|---|---|---|---|
| 2003/0025874 A1* | 2/2003 | Williams et al. | 351/200 |
| 2007/0046948 A1* | 3/2007 | Podoleanu et al. | 356/497 |
| 2007/0133372 A1* | 6/2007 | Hirai | 369/112.01 |
| 2007/0273830 A1 | 11/2007 | Levine | |
| 2008/0218694 A1* | 9/2008 | Chen et al. | 351/206 |
| 2008/0225228 A1 | 9/2008 | Saito | |
| 2009/0022378 A1* | 1/2009 | Nemoto | 382/131 |
| 2010/0149490 A1* | 6/2010 | Olivier et al. | 351/206 |

FOREIGN PATENT DOCUMENTS

| | | |
|---|---|---|
| GB | 2429522 A | 2/2007 |
| JP | 2001-000395 A | 1/2001 |
| JP | 2007-089828 A | 4/2007 |
| JP | 2007-515220 A | 6/2007 |
| JP | 2007-330585 A | 12/2007 |
| JP | 2008-161406 A | 7/2008 |
| WO | 03/020121 A1 | 3/2003 |

OTHER PUBLICATIONS

Fernandez et al, Three-dimensional Adaptive Optics Ultrahigh-Resolution Optical Coherence Tomography Using a Liquid Crystal Spatial Light Modulator, pp. 3432-3444, Vision Research 45, 2005, XP027298129.

Y.Zhang et al, "High-speed volumetric imaging of cone photoreceptors with adaptive optics spectral-domain optical coherence tomography", Optics Express, vol. 14, No. 10, May 15, 2006.

* cited by examiner

*Primary Examiner* — Dawayne A Pinkney
(74) *Attorney, Agent, or Firm* — Canon USA Inc IP Division (57) ABSTRACT

An adaptive optics apparatus includes an aberration measuring unit that measures an aberration caused by a test object, the aberration being measured on the basis of returning light that returns from the test object; an aberration correcting unit that performs aberration correction in accordance with the aberration measured by the aberration measuring unit; an irradiation unit that irradiates the test object with light corrected by the aberration correcting unit; and an acquiring unit that acquires information based on a transmittance of the test object on the basis of the aberration measured by the aberration measuring unit.

58 Claims, 7 Drawing Sheets

ADAPTIVE OPTICS APPARATUS, ADAPTIVE OPTICS METHOD, AND IMAGING APPARATUS

BACKGROUND OF THE INVENTION

1. Field of the Invention

The present invention relates to a method for controlling an optical imaging apparatus including an adaptive optics system. The present invention also relates to a program, a storage medium, and an optical imaging apparatus for implementing the method.

In particular, the present invention relates to a method for controlling an ocular-fundus imaging apparatus having a function of measuring and correcting an aberration of a subject's eye and being capable of obtaining images of the subject's eye at a plurality of resolutions. The present invention also relates to the optical imaging apparatus.

2. Description of the Related Art

Recently, scanning laser ophthalmoscopes (SLO) which two-dimensionally irradiate a fundus with a laser beam and receive light reflected by the fundus and imaging apparatuses using interference of low-coherence light have been developed as ophthalmologic imaging apparatuses.

The imaging apparatuses using the interference of low-coherence light is called optical coherence tomography (OCT) apparatuses, and is used, in particular, to obtain a tomographic image of a fundus or an area around the fundus.

Various types of OCT, such as time domain OCT (TD-OCT) and spectral domain OCT (SD-OCT), have been developed.

In the ophthalmologic imaging apparatuses, recently, the numerical aperture (NA) of the laser has been increased, and the resolution has been increased accordingly.

However, in the process of obtaining an image of a fundus, the fundus is irradiated with a laser beam through optical tissues, such as a cornea and a lens, of an eye.

As the resolution increases, the influence of an aberration of the cornea and the lens on the quality of the obtained image increases.

Accordingly, researches on adaptive optics SLO (AO-SLO) and adaptive optics OCT (AO-OCT) have been conducted. In AO-SLO and AO-OCT, an adaptive optics (AO) system, which is an adaptive optics system for measuring and correcting an aberration of the eye, is adopted. An example of AO-OCT is described in Optics Express, Vol. 14, No. 10, 15 May 2006, by Y. Zhang et al. In AO-SLO and AO-OCT, a wavefront of an eye is generally measured by a Shack-Hartmann wavefront sensor method.

In the Shack-Hartmann wavefront sensor method, the wavefront is measured by causing measurement light to be incident on the eye and receiving light reflected by the eye with a CCD camera through a microlens array. In AO-SLO and AO-OCT, a high-resolution image can be obtained by driving components such as a deformable mirror and a spatial phase modulator so as to correct the measured wavefront and obtaining an image of a fundus through the components. In general, when the NA of the laser is increased to increase the resolution, the amount of aberration caused by the optical tissues, such as the cornea and the lens, of the eye increases accordingly.

The aberration is corrected by the above-described AO. However, there is a limit to the amount by which the wavefront can be corrected by the deformable mirror or the spatial phase modulator. Therefore, there is a risk that the aberration cannot be appropriately corrected depending on the subject's eye.

SUMMARY OF THE INVENTION

If the aberration cannot be appropriately corrected, high-resolution imaging cannot be performed. In addition, the intensity of signal light received by the sensor decreases, and imaging sensitivity is reduced compared to that in the case where an imaging operation is performed at a low resolution.

In addition, according to the related art, a user cannot know whether the aberration correction is appropriately performed at a resolution set in the imaging operation. Therefore, the user must evaluate the state of correction from an obtained image, which requires a skill.

In addition, it is difficult to select an appropriate resolution for the subject's eye.

In light of the above-described problems, the present invention provides a method for controlling an optical imaging apparatus including an adaptive optics system, the method allowing an image of a test object to be obtained at an appropriate resolution in accordance with the aberration caused by the test object. The present invention also provides a program, a storage medium, and an optical imaging apparatus for implementing the method. The present invention provides a method for controlling an optical imaging apparatus including an adaptive optics system, a program, a storage medium, and an optical imaging apparatus having the following structure.

An adaptive optics apparatus according to an aspect of the present invention includes an aberration measuring unit that measures an aberration caused by a test object, the aberration being measured on the basis of returning light that returns from the test object; an aberration correcting unit that performs aberration correction in accordance with the aberration measured by the aberration measuring unit; an irradiation unit that irradiates the test object with light corrected by the aberration correcting unit; and an acquiring unit that acquires information based on a transmittance of the test object on the basis of the aberration measured by the aberration measuring unit.

Thus, according to the embodiments of the present invention, a method for controlling an optical imaging apparatus including an adaptive optics system is provided, the method allowing an image of a test object to be obtained at an appropriate resolution in accordance with the aberration caused by the test object. In addition, a program, a storage medium, and an optical imaging apparatus for implementing the method are also provided.

Further features of the present invention will become apparent from the following description of exemplary embodiments with reference to the attached drawings.

DESCRIPTION OF THE EMBODIMENTS

Embodiments of the present invention will now be described. However, the present invention is not limited to the structures of the embodiments described below.

First Embodiment

An optical imaging apparatus and a method for controlling the optical imaging apparatus in which an optical image of a test object is obtained by an SLO including an adaptive optics system according to a first embodiment of the present invention will be described with reference to FIG. 1.

According to the present embodiment, the test object, which is a measurement object, is an eye, and an image of a fundus of the eye is obtained while correcting an aberration caused by the eye with the adaptive optics system.

Figure 1:
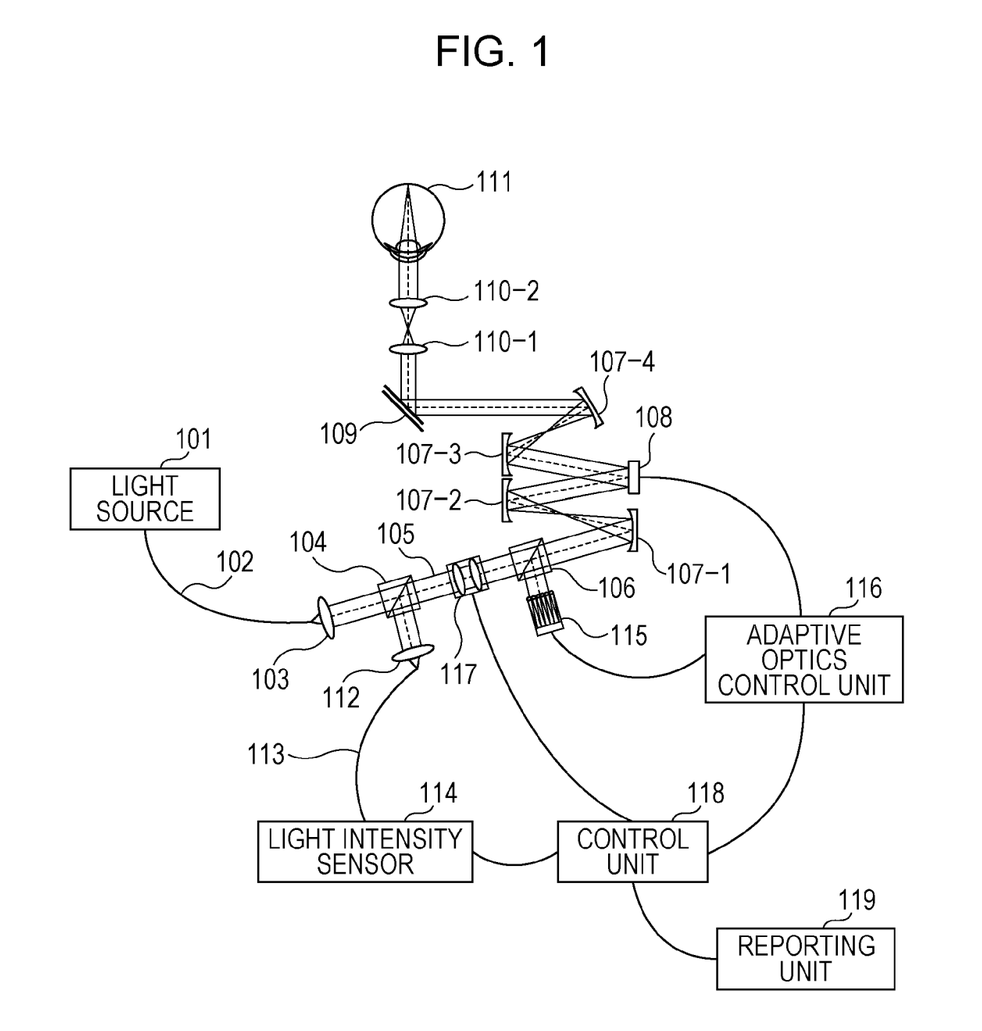
FIG. 1 is a schematic diagram illustrating the structure of an optical imaging apparatus including an SLO provided with an adaptive optics system according to a first embodiment of the present invention.

Referring to FIG. 1, in the present embodiment, a light source 101 is a superluminescent diode (SLD) with a wavelength of 840 nm.

The wavelength of the light source 101 is not particularly limited. However, in an apparatus for obtaining an image of a fundus, the wavelength can be set in the range of 800 nm to 1,500 nm to reduce glare for a subject and maintain the resolution.

Although the SLD is used in the present embodiment, a laser, for example, may instead be used.

In the present embodiment, the SLD is used as a common light source for both obtaining the image of the fundus and measuring a wavefront. However, separate light sources may be used, and light rays from the respective light sources may be combined together at an intermediate position.

Light emitted from the light source 101 travels through a single-mode optical fiber 102, is collimated by a collimator 103, and is emitted as collimated light.

Measurement light 105 emitted from the collimator 103 passes through a light splitting unit 104 and is incident on a resolution setting unit 117. The resolution setting unit 117 changes an imaging resolution by changing a beam diameter of a beam incident thereon and then emitting the beam.

The resolution setting unit 117 is controlled in accordance with a resolution change command transmitted from a control unit 118.

A beam splitter or the like can be used as the light splitting unit 104. The resolution setting unit 117 may include a plurality of lenses, and be structured such that the positional relationship between the lenses can be adjusted. The measurement light passes through the resolution setting unit 117 and is guided to the adaptive optics system.

The adaptive optics system includes a light splitting unit 106, a wavefront sensor 115, a wavefront correction device 108, and reflection mirrors 107-1 to 107-4.

The reflection mirrors 107-1 to 107-4 are arranged such that at least the pupil of the eye is optically conjugate with the wavefront sensor 115 and the wavefront correction device 108. A beam splitter or the like can be used as the light splitting unit 106.

In the present embodiment, a deformable mirror is used as the wavefront correction device 108, which functions as an aberration correcting unit.

The deformable mirror is capable of locally changing a light reflection direction thereof. Various types of deformable mirrors are in practical use.

Figure 3A:
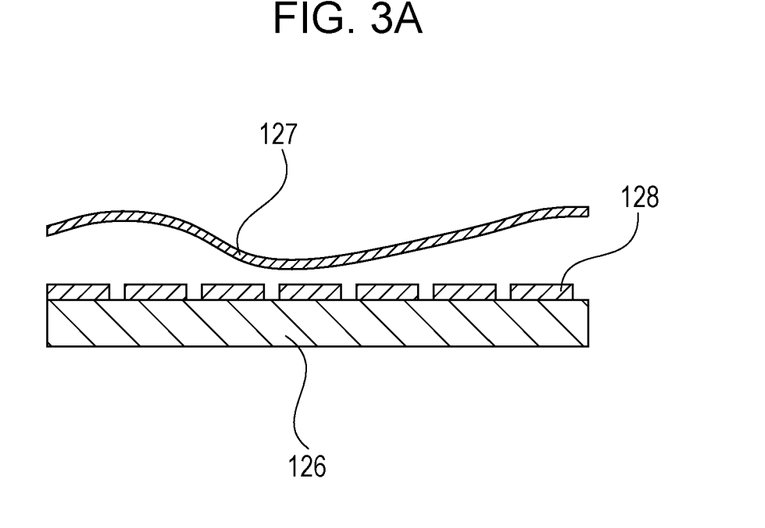
FIG. 3A is a schematic diagram illustrating a deformable mirror as an example of a wavefront correction device according to the first embodiment of the present invention.

The deformable mirror is, for example, a device having a sectional view illustrated in FIG. 3A.

The device includes a film-shaped deformable mirror surface 127 that reflects incident light, a base portion 126, actuators 128 disposed between the mirror surface 127 and the base portion 126, and a support member (not shown) that supports the mirror surface 127 at the periphery thereof.

With regard to the principle of operation of the actuators 128, the actuators 128 may be operated using electrostatic force, magnetic force, piezoelectric effect, etc., and the structure of the actuators 128 differs depending on the principle of operation thereof.

The actuators 128 are two-dimensionally arranged on the base portion 126, and are selectively driven so that the shape of the mirror surface 127 can be changed.

Figure 3B:
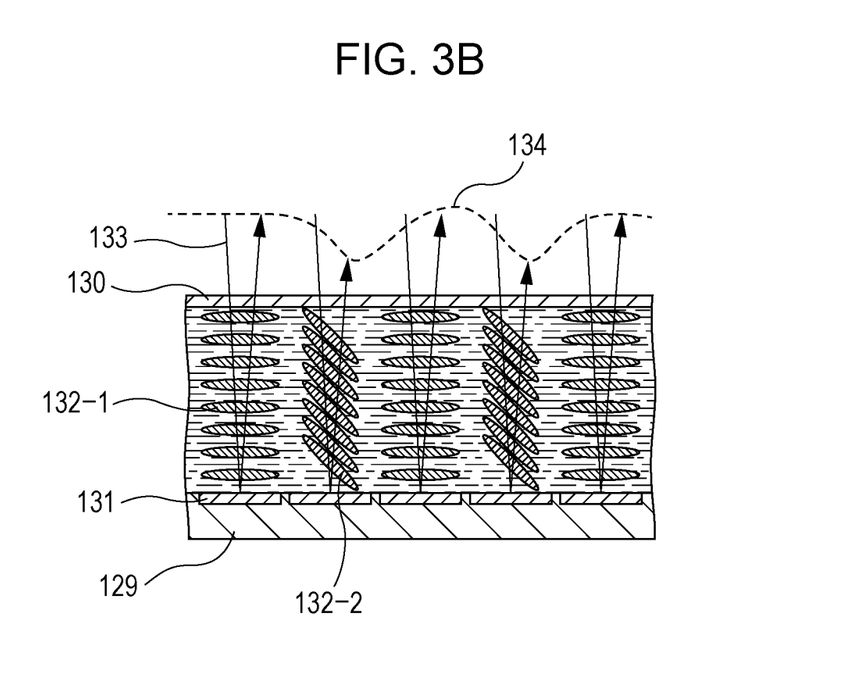
FIG. 3B is a schematic diagram illustrating a reflective liquid-crystal light modulator as another example of the wavefront correction device according to the first embodiment of the present invention.

A spatial phase modulator including a liquid crystal element is another example of the wavefront correction device 108. FIG. 3B is a schematic diagram illustrating a reflective liquid-crystal light modulator.

This spatial phase modulator is structured such that liquid crystal molecules 132-1 and 132-2 are enclosed in a space surrounded by a base portion 129 and a cover 130. A plurality of pixel electrodes 131 are provided on the base portion 129, and a transparent counter electrode (not shown) is provided on the cover 130.

When no voltage is applied between the electrodes, the liquid crystal molecules are oriented similarly to the liquid crystal molecules denoted by 132-1. When a voltage is applied, the liquid crystal molecules are oriented similarly to the liquid crystal molecules denoted by 132-2. Accordingly, the refractive index of the incident light changes in accordance with the orientation of the liquid crystal molecules.

The phase can be spatially modulated by changing the refractive index at each of the pixels by controlling the voltage applied to each of the pixel electrodes 131.

For example, in the case where light 133 is incident on the element, the phase of a light component that passes through the liquid crystal molecules 132-2 is delayed with respect to the phase of a light component that passes through the liquid crystal molecules 132-1. As a result, a wavefront 134 illustrated in FIG. 3B is formed.

Since the liquid crystal element has a polarization property, the liquid crystal element is generally provided with a polarizing element or the like for adjusting the polarization of the incident light.

The light that has passed through the adaptive optics system is one-dimensionally or two-dimensionally scanned by a scanning optical system 109.

In the present embodiment, the scanning optical system 109 includes two galvano scanners for scanning the light in a main scanning direction (horizontal direction of the fundus) and a sub-scanning direction (vertical direction of the fundus).

To achieve high-speed imaging operation, a resonance scanner may instead be used in the scanning optical system 109 for scanning the light in the main scanning direction.

Depending on the structure of the scanning optical system 109, an optical system including mirrors and lenses may be disposed between the scanners so as to set the scanners in the scanning optical system 109 to an optically conjugate state.

The measurement light scanned by the scanning optical system 109 is incident on an eye 111 through ocular lenses 110-1 and 110-2.

The measurement light incident on the eye 111 is reflected and diffused by the fundus. The eye 111 can be appropriately irradiated with the measurement light in accordance with the visibility thereof by adjusting the positions of the ocular lenses 110-1 and 110-2.

Although lenses are included in the eyepiece section in the present embodiment, spherical mirrors or the like may be used instead.

The light reflected and diffused by a retina of the eye 111 travels in the reverse direction along the same path as the path along which the light has traveled to the eye 111, and is split by the light splitting unit 106 such that a portion of the light is reflected toward the wavefront sensor 115 and is used to measure the wavefront of the light.

Figure 3C:
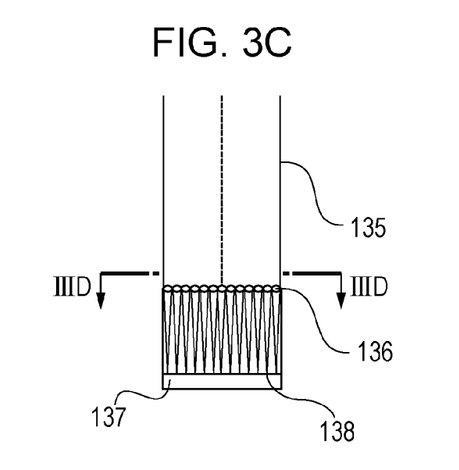
FIGS. 3C and 3D are schematic diagrams illustrating the structure of a Shack-Hartmann sensor as an example of a wavefront sensor according to the first embodiment of the present invention.
Figure 3D:
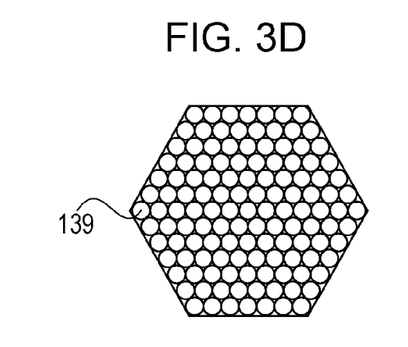

In the present embodiment, a Shack-Hartmann sensor illustrated in FIGS. 3C and 3D is used as the wavefront sensor 115.

Referring to FIG. 3C, the wavefront of a light ray 135 is measured. The light ray 135 is caused to pass through the microlens array 136, and is collected on a focal plane 138 of a CCD sensor 137. FIG. 3D is a sectional view of FIG. 3C taken along line IIID-IIID, which illustrates the structure of microlenses 139 included in the microlens array 136.

The light ray 135 is collected on the CCD sensor 137 through the microlenses 139. Therefore, the light ray 135 is collected at the same number of spots as the number of microlenses 139.

Figure 3E:
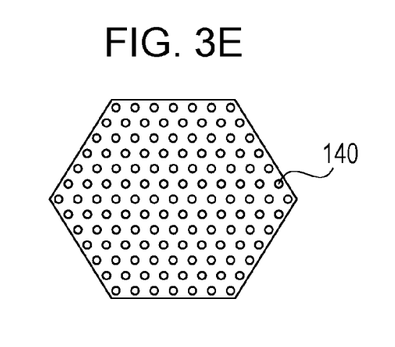
FIG. 3E is a schematic diagram illustrating the state in a light ray of which a wavefront is measured is collected on a CCD sensor according to the first embodiment of the present invention.

FIG. 3E illustrates the state in which the light ray 135 of which the wavefront is measured is collected on the CCD sensor 137. The light ray 135 passes through the microlenses 139 and is collected at spots 140.

Figure 3F:
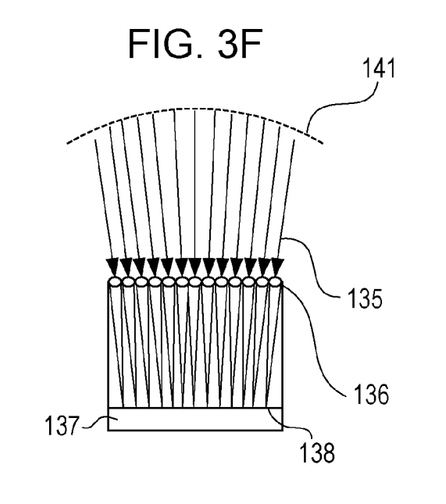
FIGS. 3F and 3G are schematic diagrams illustrating a case in which a wavefront having a spherical aberration is measured according to the first embodiment of the present invention.

The wavefront of the incident light ray 135 is calculated from the positions of the spots 140. For example, FIGS. 3F and 3G illustrate a case in which a wavefront having a spherical aberration is measured.

Here, it is assumed that the light ray 135 has a wavefront denoted by 141. The light ray 135 is collected by the microlens array 136 at positions corresponding to normal directions of local areas of the wavefront.

Figure 3G:
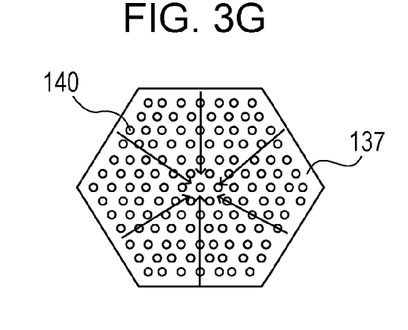

The state in which the light ray 135 is collected on the CCD sensor 137 in this case is illustrated in FIG. 3G.

Since the light ray 135 has a spherical aberration, the spots 140 are displaced toward the center. The wavefront of the light ray 135 can be determined by calculating the positions of the spots 140.

Although a Shack-Hartmann sensor is used as the wavefront sensor in the present embodiment, the wavefront sensor is not limited to this. For example, other wavefront measuring units, such as a curvature sensor, or a method of performing a reverse calculation based on focused point images may be used instead.

The reflected and diffused light that has passed through the light splitting unit 106 is split by the light splitting unit 104 such that a portion thereof is guided toward a photodetector 114 through a collimator 112 and an optical fiber 113.

The light is converted into electric signals by the photodetector 114, and is reconstructed into a fundus image by the control unit 118.

The wavefront sensor 115 is connected to an adaptive optics control unit 116. The wavefront sensor 115 transmits the wavefront of the received light ray to the adaptive optics control unit 116.

The wavefront correction device (deformable mirror) 108 is also connected to the adaptive optics control unit 116. The deformable mirror 108 deforms into a shape specified by the adaptive optics control unit 116.

The adaptive optics control unit 116 calculates a shape with which the waveform can be corrected to a waveform without an aberration on the basis of the waveform transmitted from the wavefront sensor 115, and commands the deformable mirror 108 to deform into the calculated shape.

Feedback control is performed such that an optimum wavefront can be continuously formed by repeating the processes of measuring the wavefront and commanding the deformable mirror to deform. Alternatively, open-loop control is performed in which a command is transmitted to the deformable mirror only once after the wavefront is measured. The result of the correction (information based on a transmittance of a test object acquired on the basis of the aberration measured by an aberration measuring unit) is reported to the control unit (control system) 118 from the adaptive optics control unit 116, and is then reported to the user by a reporting unit 119. The result of the correction is acquired by an acquiring unit (not shown). The test object is, for example, an anterior segment of the subject's eye, and the reporting unit 119 can report a symptom or the like of the anterior segment (e.g., cataract) of the subject's eye.

The reporting unit 119 displays information on a display screen. The reported information includes information of a wavefront aberration, which is a measurement result obtained by the Shack-Hartmann sensor 115.

The reported information may further include light intensity measured by the photodetector 114 and a drive amount of the correction device. In addition to current values of the above-mentioned parameters, variations with time thereof can be reported, and it can also be reported whether or not a parameter has reached a predetermined threshold.

In the present embodiment, the control system 118 controls the resolution setting unit 117 (a changing unit that changes the diameter of light from the light source on the basis of the aberration measured by the aberration measuring unit) so as to change the resolution in accordance with the correction result. The changing unit can reduce the diameter of the light from the light source when at least one of the amount of the aberration measured by the aberration measuring unit and the transmittance satisfies a predetermined condition. More specifically, the changing unit can reduce the diameter of the light from the light source when at least one of the amount of the aberration and the transmittance is larger than a predetermined value after a predetermined time interval from the start of the correction performed by the aberration correcting unit. In the case where the test object is the anterior segment of the subject's eye, a portion having a low transmittance in the anterior segment of the subject's eye can be irradiated with the light whose diameter is changed by the changing unit.

When the resolution is changed, the measured aberration varies. Accordingly, feedback control of the deformable mirror 108 is performed so as to correct the aberration that varies.

Next, the method for controlling the optical imaging apparatus according to the present embodiment will be described with reference to a flowchart shown in FIG. 4.

First, the control process is started in step S101. Then, a resolution is set in step S102.

More specifically, the control unit 118 sets the resolution by controlling the resolution setting unit 117 so as to change the beam diameter of the measurement light.

In this step, the resolution may be set to, for example, a highest resolution that can be set by the apparatus, a lowest resolution that can be set by the apparatus, or a middle resolution between the highest and lowest resolutions.

In the basic process performed by the adaptive optics system, while the eye 111 is irradiated with the measurement light from the light source 101, the aberration is measured by the wavefront sensor 115 in step S103. Then, in step S105, the amount of correction is calculated by the adaptive optics control unit 116.

Then, the correction device 108 is driven under the control of the adaptive optics control unit 116 in step S106. These steps are repeatedly performed.

After the aberration is measured in step S103, in step S104, the control unit 118 determines whether or not the amount of aberration is smaller than a reference value (also called a predetermined value), that is, whether or not the aberration correction is appropriately performed.

The reference value may be specific to the apparatus. Alternatively, the reference value may be set by the user.

If the amount of aberration is greater than or equal to the reference value, step S105 and the following steps are performed. In step S107, the control unit 118 determines whether or not the limit of aberration correcting ability of the wavefront correction device 108 has been reached.

More specifically, it is determined that the limit of the correcting ability has been reached when an aberration change rate is smaller than a reference value or when the drive amount of the correction device is at a maximum.

If it is determined that the limit of the correcting ability has not been reached in step S107, the process returns to step S103 and the above-described steps are repeated.

If it is determined that the limit of the correcting ability has been reached in step S107, the process proceeds to step S112 and the control unit 118 causes the reporting unit 119 to report the correction result.

In this case, it is reported that sufficient correcting ability cannot be provided when the resolution is set to the current resolution.

Then, in step S113, it is determined whether or not the currently set resolution is equal to the lowest resolution that can be set by the apparatus.

If the currently set resolution is equal to the lowest resolution, the process proceeds to step S110 and the imaging operation for obtaining a fundus image is performed under the control of the control unit 118. Then, the process is terminated in step S111.

In this case, the imaging operation is performed at the lowest resolution that can be set by the apparatus.

If the currently set resolution is not equal to the lowest resolution, the process proceeds to step S114 and the control unit 118 controls the resolution setting unit 117 so as to reduce the resolution. Then, the process returns to step S103 and the steps for correcting the aberration are repeated.

In the case where the amount of aberration is smaller than the reference value in step S104, the process proceeds to step S108, where it is reported that the amount of aberration is smaller than the reference value. Then, the process proceeds to step S109.

In step S109, it is determined whether or not the currently set resolution is equal to the highest resolution that can be set by the apparatus. If the currently set resolution is equal to the highest resolution, the process proceeds to step S110 and the imaging operation for obtaining a fundus image is performed. Then, the process is terminated in step S111.

In this case, the imaging operation is performed at the highest resolution that can be set by the apparatus.

If it is determined that the currently set resolution is not equal to the highest resolution that can be set by the apparatus in step S109, the process proceeds to step S115.

In step S115, it is determined whether or not a resolution changing process has previously been performed. If the resolution changing process has previously been performed, it is determined whether or not the resolution was previously reduced.

If the above-mentioned condition is not satisfied, the process proceeds to step S116, where the resolution is increased. Then, the process returns to step S103, and the steps for correcting the aberration are repeated.

If the above-mentioned condition is satisfied in step S115, that is, when the resolution is set to an optimum value for the measured aberration, the process proceeds to step S110, where the imaging operation for obtaining a fundus image is performed. Then, the process is terminated in step S111.

As an example, a case in which a low resolution is set in step S102 and an imaging operation for obtaining an image of a subject's eye is performed will be described. Here, it is assumed that the subject's eye causes an aberration that can be measured with an intermediate resolution of the apparatus.

First, the resolution is set to the lowest resolution in step S102, and the aberration is measured in step S103. The aberration is not yet corrected at this time, and therefore the amount of aberration is greater than the reference value in step S104.

In steps S105 and S106, the actual correction process is performed in which the amount of correction is calculated and the wavefront correction device 108 is driven. In step S107, the condition is not yet satisfied. Therefore, the process returns to step S103, and step S103 and the following steps are repeated.

As the steps are repeated, the aberration decreases, and it is determined in step S104 that the amount of aberration is smaller than the reference value. Accordingly, the result of the determination is reported, and the process proceeds to step S109.

Since the resolution is not set to the highest resolution, the process proceeds to step S115 from step S109, and then proceeds to step S116. In step S116, the resolution is increased by a certain amount and the process returns to step S103.

Then, when steps S103 to S107 are repeated several times, it is again determined that the amount of aberration is smaller than the reference value in step S104. Therefore, steps S108 to S116 are performed again, and the resolution is further increased. Then, the process returns to step S103.

After the above-described cycle is repeated several times, the amount of correction performed by the wavefront correction device 108 reaches the limit thereof, and the condition of step S107 is satisfied.

The result the determination in step S107 is reported in step S112, and the resolution is reduced by a certain amount in step S114. Then, the process returns to step S103. Then, when steps S103 to S107 are repeated several times, it is again determined that the amount of aberration is smaller than the reference value in step S104. Therefore, the process proceeds to step S115 through steps S108 and S109.

At this time, the determination condition of step S115 is satisfied. Therefore, the imaging operation is performed in step S110, and the process is terminated in step S111.

Although the resolution is set to a low resolution when the process is started in the above-described example, the resolution may instead be set to a high resolution when the process is started. Alternatively, the resolution can be set to an intermediate resolution of the apparatus. In the present embodiment, the process is terminated in step S111 after the imaging operation is performed in step S110. However, in the case where the imaging operation for obtaining an image of the fundus is to be successively performed, the process returns to step S103 from step S110 and the steps of setting the resolution and performing the imaging operation may be repeated.

Thus, according to the present embodiment, the imaging operation can be performed at an appropriate resolution on the basis of the aberration caused by the subject's eye and the performance of the apparatus.

Second Embodiment

An optical imaging apparatus and a method for controlling the optical imaging apparatus in which an optical image is obtained by an OCT apparatus including an adaptive optics system according to a second embodiment of the present invention will be described with reference to FIG. 2.

Figure 2:
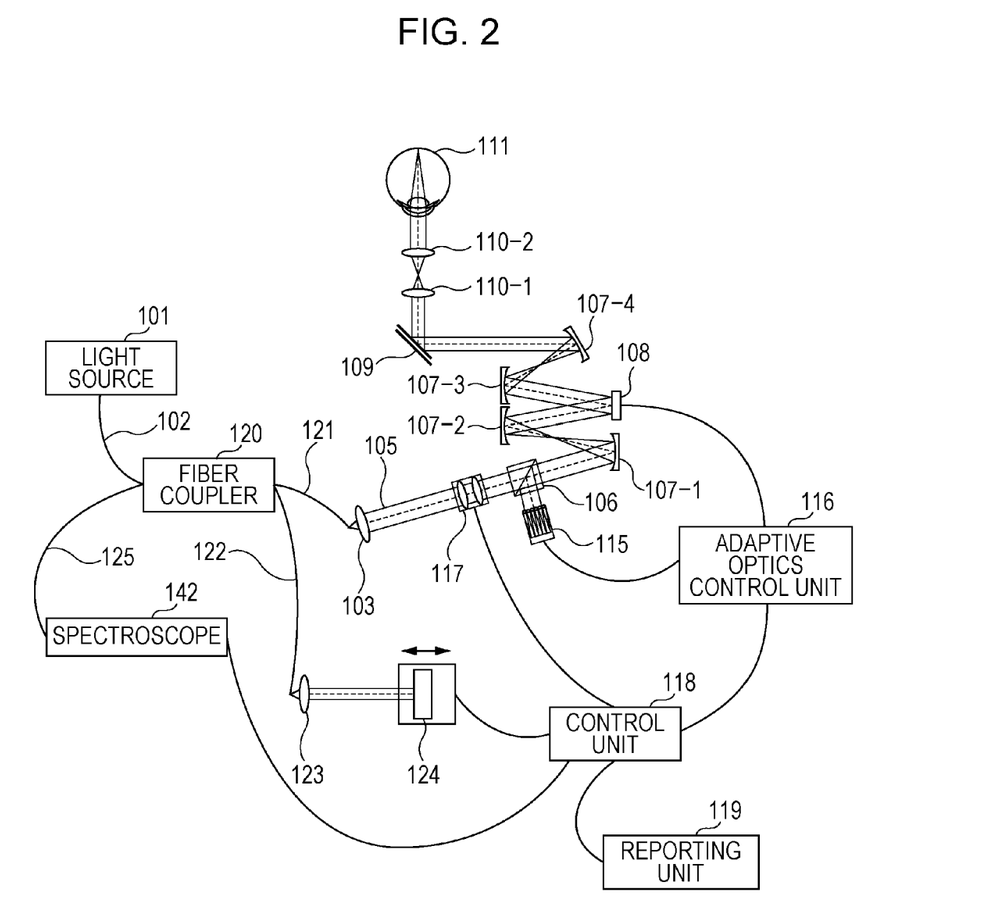
FIG. 2 is a schematic diagram illustrating the structure of an optical imaging apparatus including an OCT apparatus provided with an adaptive optics system according to a second embodiment of the present invention.

Referring to FIG. 2, a light source 101 is an SLD with a wavelength of 840 nm. The light source 101 is not particularly limited as long as the light source 101 has a low coherence, and an SLD with a wavelength range of 30 nm or more can be used.

Alternatively, an ultrashort pulse laser, such as a titanium-sapphire laser, may be used as the light source 101.

Light emitted from the light source 101 travels through a single-mode optical fiber 102 and is guided to a fiber coupler 120.

The fiber coupler 120 divides a path of the light into a signal light path 121 and a reference light path 122. A branching ratio of the fiber coupler 120 is 10:90, and 10% of the light that reaches the fiber coupler 120 is caused to enter the signal light path 121.

The light that travels through the signal light path 121 is collimated by a collimator 103, and is emitted as collimated light. The section downstream of the collimator 103 is similar to that in the first embodiment. More specifically, the light passes through the adaptive optics system and the scanning optical system, and is incident on the eye 111. Then, light reflected and diffused by the eye 111 travels along the same path as the path along which the light has traveled to the eye 111, and is guided to the fiber coupler 120 through the signal light path 121.

The reference light that travels through the reference light path 122 is emitted from a collimator 123, is reflected by a light-path-length changing unit 124, and returns to the fiber coupler 120.

The signal light and the reference light that reach the fiber coupler 120 are combined together. The combined light is guided to a spectroscope 142 through an optical fiber 125.

A tomographic image of the fundus is formed by a control unit 118 on the basis of interference light information obtained by the spectroscope 142. The control unit 118 controls the light-path-length changing unit 124 so that an image at a desired depth can be obtained.

Similar to the first embodiment, the wavefront is measured by a wavefront sensor 115, and a wavefront correction device 108 is driven so as to cancel the wavefront aberration.

Similar to the first embodiment, the result of the correction is reported and the resolution is changed. Accordingly, the imaging operation can be performed at an appropriate resolution on the basis of the aberration caused by the subject's eye and the performance of the apparatus.

In the OCT apparatus, a plurality of tomographic images (B scan) or plane images (C scan) can be successively obtained. Alternatively, a three-dimensional image can be obtained. In such a case, the process according to the present embodiment can be repeated.

Although tomographic images can be obtained by the OCT apparatus, if the NA of the incident light is increased to increase the resolution, the depth of field decreases. Accordingly, a single tomographic image includes both focused and unfocused areas.

Accordingly, in the imaging operation, an imaging range in the depth direction can be divided into sections having a dimension corresponding to the depth of field (in other words, a plurality of tomographic images may be obtained at different positions in the depth direction), and then images at different depths may be combined so that a tomographic image that is focused over the entire area can be obtained.

Figure 4:
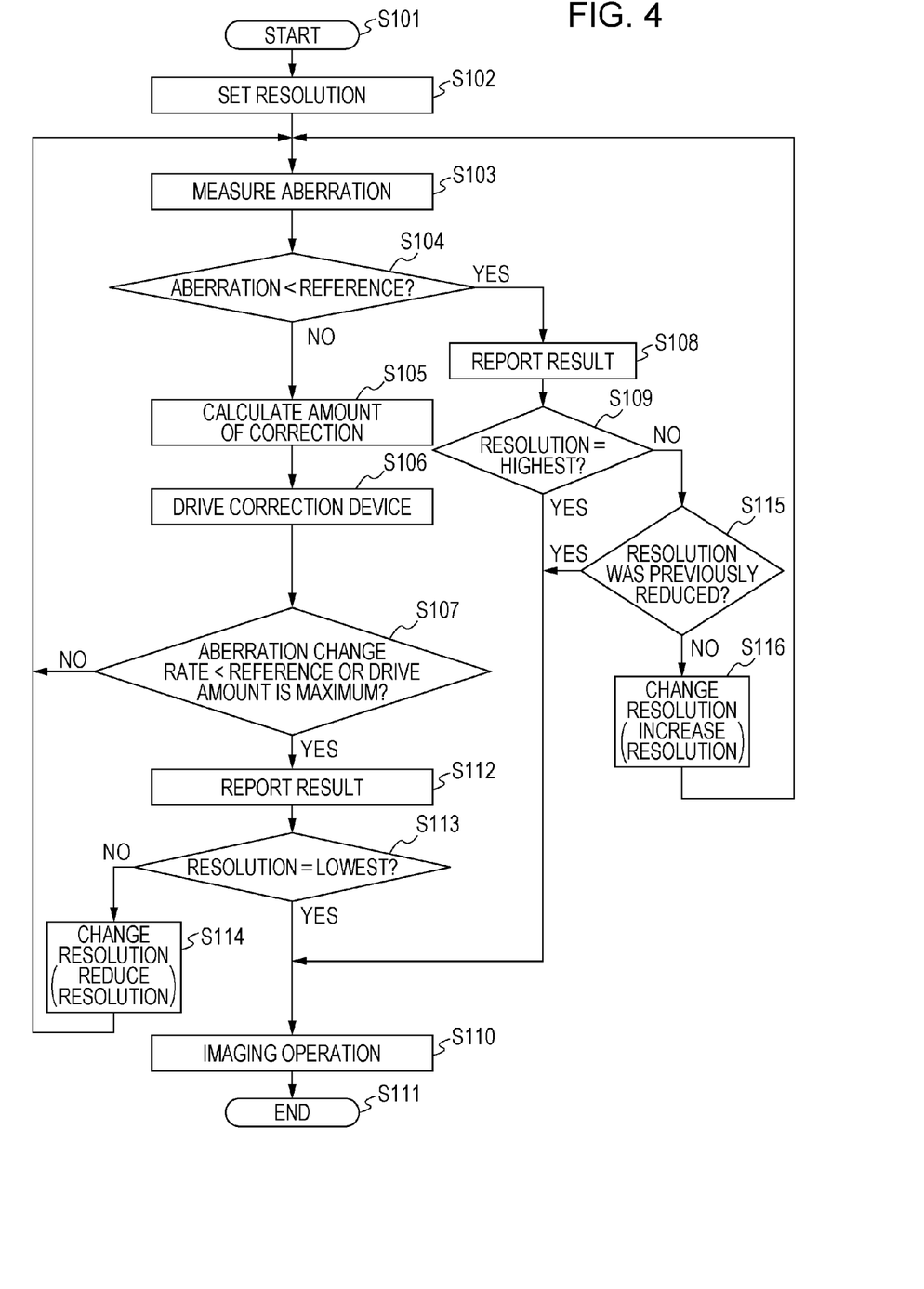
FIG. 4 is a flowchart illustrating an example of control steps performed by the optical imaging apparatus according to the first embodiment of the present invention.

In such a case, the imaging range in the depth direction in each cycle of the imaging operation may be changed (that is, from a first position to a second position that differs from the first position in the depth direction) in accordance with the resolution changed in steps S114 and S116 in FIG. 4. Accordingly, an image having a large focused area can be quickly obtained.

Third Embodiment

Figure 5:
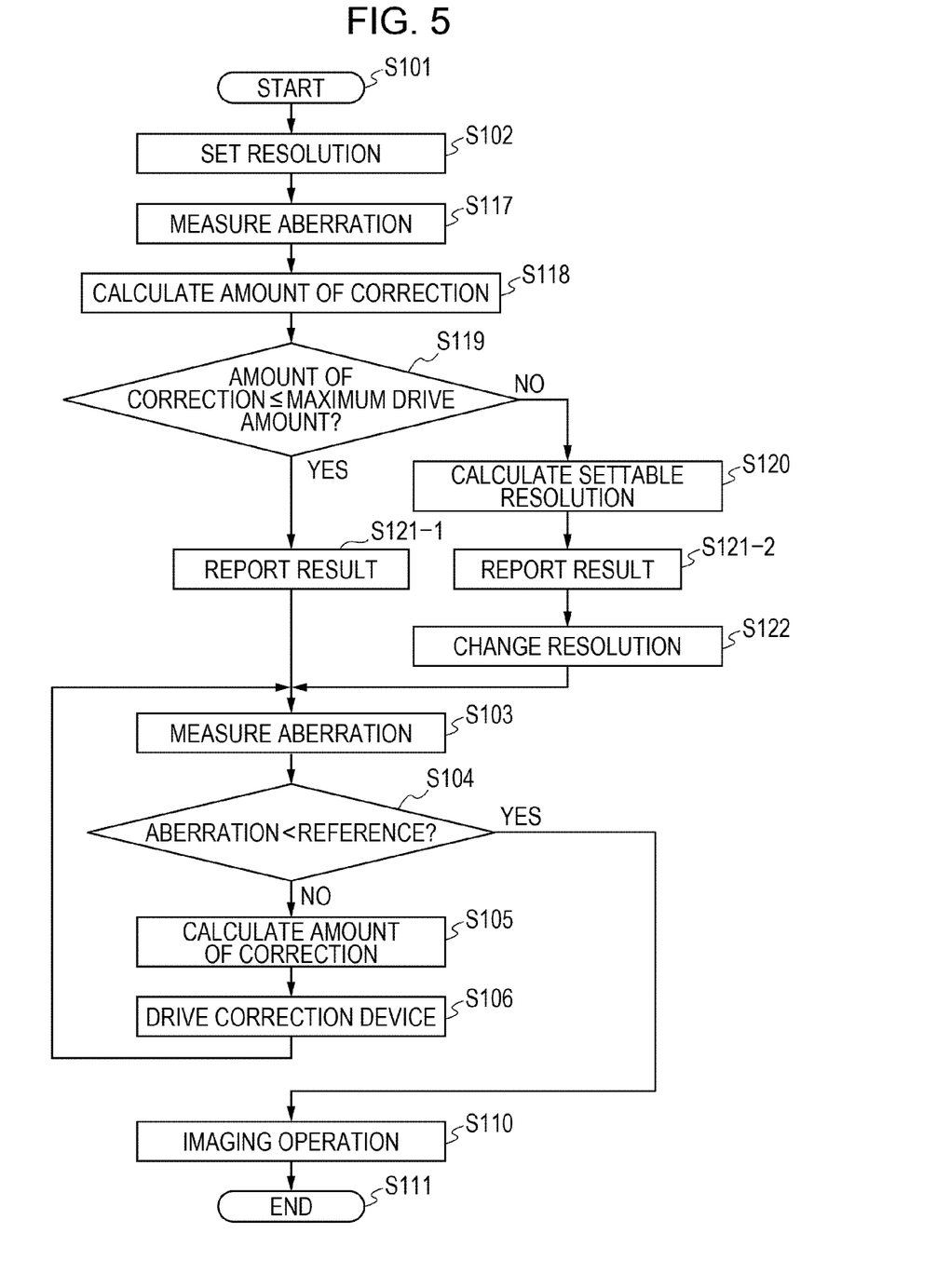
FIG. 5 is a flowchart illustrating an example of control steps performed by an optical imaging apparatus according to a third embodiment of the present invention.

A method for controlling an optical imaging apparatus including an SLO provided with an adaptive optics system according to a third embodiment of the present invention that differs from that of the first embodiment will be described with reference to a flowchart shown in FIG. 5.

The basic structure of the present embodiment is similar to that of the first embodiment.

First, the control process is started in step S101. Then, a resolution is set in step S102. Here, the resolution is set to a highest resolution that can be set by the apparatus. In other words, the beam diameter is set to the largest incident beam diameter.

The largest incident beam diameter is set so that the aberration of the entire pupil area can be measured.

In step S117, the aberration is measured by the wavefront sensor 115.

As described above, the aberration of the entire pupil area is measured. The amount of correction is calculated by the control unit 118 in step S118 on the basis of the aberration measured in step S117. In step S119, the amount of correction is compared with the maximum drive amount of the wavefront correction device 108.

If the amount of correction is smaller than or equal to the maximum drive amount, it is determined that the correction can be performed at the set resolution. Accordingly, the result of the determination is reported by the reporting unit 119 in step S121-1, and the process proceeds to step S103. If the amount of correction is greater than the maximum drive amount, it is determined that sufficient correcting ability cannot be provided at the set resolution. Accordingly, the process proceeds to step S120.

The maximum drive amount used as a criterion in above-described determination may be set to a maximum value of a drive amount of the device itself. However, the maximum drive amount may instead be set to a numerical value including an allowance to allow an error in the correction control.

In step S120, the control unit 118 calculates a pupil diameter for which the correction can be performed on the basis of the information of the measured aberration.

The calculation result is reported in step S121-2, and the resolution is changed in accordance with the calculated pupil diameter in step S122. Then, the process proceeds to step S103.

Similar to the first embodiment, the aberration is measured in step S103, and the amount of correction is calculated in step S105 on the basis of the measurement result. Then, the correction device is driven in step S106. These steps are repeatedly performed.

After the aberration is measured in step S103, in step S104, it is determined whether or not the amount of aberration is smaller than a preset reference value.

If the amount of aberration is greater than or equal to the reference value, step S105 and the following steps are performed. Then, the process returns to step S103, and the above-described steps are repeated.

In the case where the amount of aberration is smaller than the reference value in step S104, the process proceeds to step S110, where the imaging operation for obtaining a fundus image is performed. Then, the process is terminated in step S111.

Thus, according to the process of the present embodiment, the imaging operation can be performed at an appropriate resolution by an extremely simple process.

Fourth Embodiment

Figure 6:
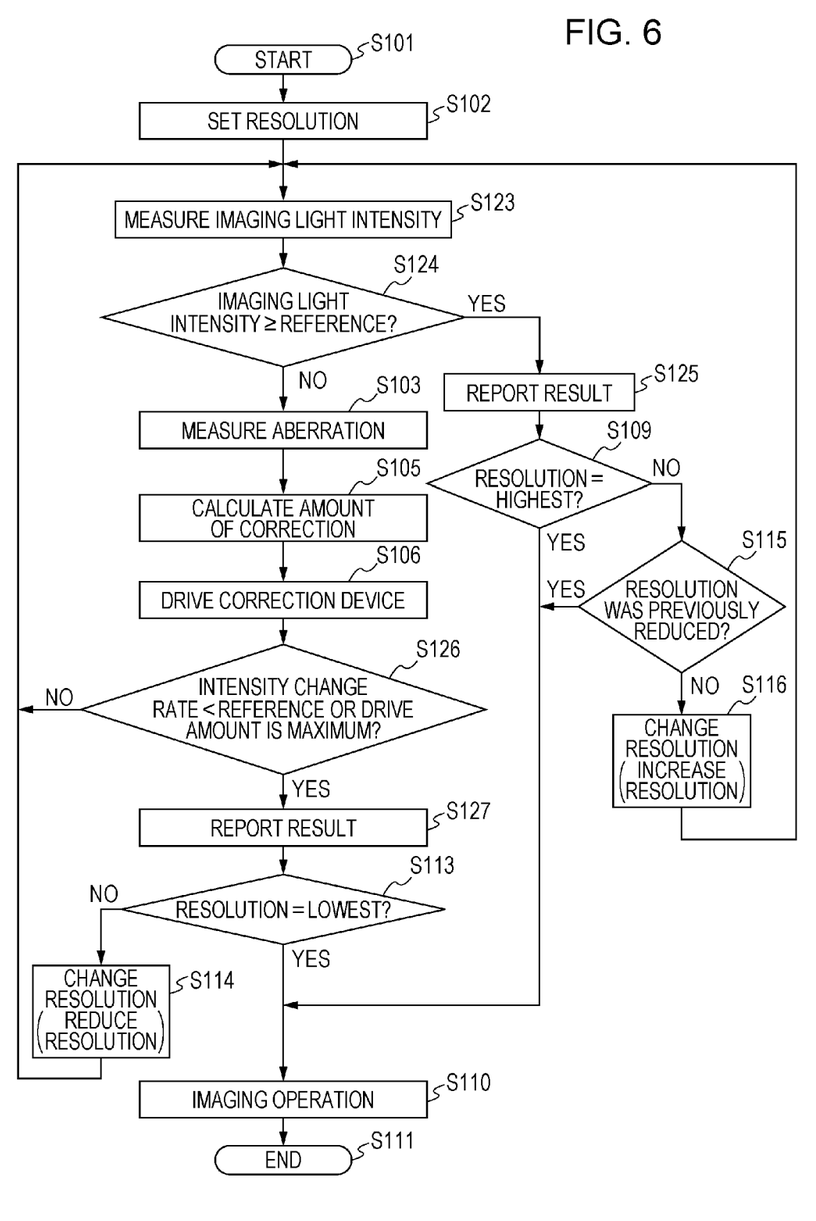
FIG. 6 is a flowchart illustrating an example of control steps performed by an optical imaging apparatus according to a fourth embodiment of the present invention.

A method for controlling an optical imaging apparatus including an SLO provided with an adaptive optics system according to a fourth embodiment of the present invention that differs from those of the first and third embodiments will be described with reference to a flowchart shown in FIG. 6.

According to the present embodiment, the intensity of the imaging light (imaging signal intensity) is reported as the result of aberration correction, and is used to determine whether or not to change the resolution.

The basic structure of the present embodiment is similar to that of the first embodiment.

First, the control process is started in step S101. Then, a resolution is set in step S102.

In this step, the resolution may be set to, for example, a highest resolution that can be set by the apparatus, a lowest resolution that can be set by the apparatus, or a middle resolution between the highest and lowest resolutions.

Next, in step S123, the intensity of the imaging light is measured.

In the present embodiment, the intensity of the imaging light is the intensity of light measured by the photodetector 114 illustrated in FIG. 1.

In step S124, the control unit 118 determines whether or not the measured intensity is greater than or equal to a reference value. The measured light intensity may directly be used for the determination. Alternatively, the average of the measurement light intensity per unit time (that is, of course, a value corresponding to a certain time interval). In addition, light reflected at a single point on the retina may be measured, or the average value of the intensity of light reflected at a certain area on the retina may be measured by driving the optical scanning system.

If it is determined in step S124 that the intensity of the imaging light is smaller than the reference value, the basic process is performed by the adaptive optics system in step S103 and the following steps.

More specifically, the aberration is measured in step S103, and the amount of correction is calculated in step S105 on the basis of the measurement result. Then, the correction device is driven in step S106.

In step S126, if the rate of change in the intensity of the measurement light is lower than a reference value or if the drive amount of the correction device is at a maximum, the correction result is reported in step S127.

This occurs when, for example, the amount of aberration is beyond the correcting ability of the correction device, or when the intensity of the imaging light is reduced due to reasons other than the aberration, such as cataract. In the case where the amount of aberration is beyond the correction ability of the correction device, it is effective to reduce the amount of aberration by reducing the resolution. In the case where the light intensity is reduced due to other reasons such as cataract, an image of the fundus can be obtained by causing an incident beam with a small beam diameter to pass through a portion with high transmittance.

Then, in step S113, it is determined whether or not the currently set resolution is equal to the lowest resolution that can be set by the apparatus. If the currently set resolution is equal to the lowest resolution, the process proceeds to step S110 and the imaging operation for obtaining a fundus image is performed. Then, the process is terminated in step S111.

In this case, the imaging operation is performed at the lowest resolution that can be set by the apparatus. If the currently set resolution is not equal to the lowest resolution, the resolution is reduced in step S114. Then, the process returns to step S123.

If it is determined in step S124 that the intensity of the imaging light is higher than the reference value, the process proceeds to step S125 and it is reported that the intensity of the imaging light is high.

Then, similar to the first embodiment, the process proceeds to step S109, where it is determined whether or not the currently set resolution is equal to the highest resolution that can be set by the apparatus.

If the currently set resolution is equal to the highest, the process proceeds to step S110 and the imaging operation for obtaining a fundus image is performed. Then, the process is terminated in step S111. In this case, the imaging operation is performed at the highest resolution that can be set by the apparatus.

If it is determined that the currently set resolution is not equal to the highest resolution that can be set by the apparatus in step S109, the process proceeds to step S115. In step S115, it is determined whether or not a resolution changing process has previously been performed. If the resolution changing process has previously been performed, it is determined whether or not the resolution was previously reduced.

If the above-mentioned condition is not satisfied, the process proceeds to step S116, where the resolution is increased. Then, the process returns to step S123 and the above-described steps are repeated.

If the above-mentioned condition is satisfied in step S115, that is, when the resolution is set to an optimum value for the measured aberration, the process proceeds to step S110, where the imaging operation for obtaining a fundus image is performed. Then, the process is terminated in step S111.

Thus, according to the present embodiment, the imaging operation can be performed at an appropriate resolution on the basis of the state of the subject's eye and the performance of the apparatus.

With regard to the methods for controlling the optical imaging apparatuses according to the above-described embodiments, programs for causing a computer to execute the control methods may also be provided. The programs may be stored in storage media, and be read by the computer.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262386 filed Nov. 17, 2009, which is hereby incorporated by reference herein in its entirety.

What is claimed is:

1. An adaptive optics apparatus comprising:
an aberration measuring unit that measures an aberration caused by an object, the aberration being measured on the basis of returning light that returns from the object;
an aberration correcting unit that performs aberration correction on the basis of a result of the aberration measured by the aberration measuring unit;
a changing unit that changes a diameter of light for irradiating the object on the basis of a result of the aberration measured by the aberration measuring unit after performing aberration correction; and
an irradiation unit that irradiates the object with the light whose diameter is changed by the changing unit.

2. The adaptive optics apparatus according to claim 1, wherein the changing unit reduces the diameter of the light from the light source in a case where an amount of the aberration measured by the aberration measuring unit after performing aberration correction satisfies a predetermined condition.

3. The adaptive optics apparatus according to claim 2, wherein the changing unit reduces the diameter of the light from the light source in a case where the amount of the aberration is larger than a predetermined value after a predetermined time interval from the start of the correction performed by the aberration correcting unit.

4. The adaptive optics apparatus according to claim 1,
wherein the object is a subject's eye, and
further comprising an acquiring unit that acquires information based on a transmittance of an anterior segment of the subject's eye.

5. The adaptive optics apparatus according to claim 4, wherein a portion having a low transmittance in the anterior segment of the subject's eye is irradiated with the light whose diameter is changed by the changing unit.

6. The adaptive optics apparatus according to claim 1, further comprising:
a reporting unit that reports a result of the aberration measured by the aberration measuring unit.

7. The adaptive optics apparatus according to claim 1, wherein light used to measure the aberration with the aberration measuring unit and light used to acquire an image of the object are emitted form different light sources.

8. an imaging apparatus, comprising:
the adaptive optics apparatus according to claim 1; and
an image acquiring unit that acquires an image of the object on the basis of light that returns from the object irradiate with the light from the irradiation means.

9. The imaging apparatus according to claim 8, further comprising:
a separating unit that separates light from a light source into light to be incident on the aberration correcting unit and reference light,
wherein the image capturing unit captures a tomographic image of the object on the basis of interference light resulting from interference between the light that returns from the object is irradiated with the light from the irradiation unit and the reference light.

10. The imaging apparatus according to claim 9, further comprising:
a starting unit that starts, in a case where the aberration measured by the aberration measuring unit satisfies a predetermined condition, an operation of acquiring the tomographic image of the object after the diameter of the light from the light source is reduced by the changing unit.

11. The adaptive optics apparatus according to claim1,
wherein the object is an eye, and
wherein the aberration measuring unit and the aberration correcting unit are positioned optically conjugate with an anterior segment of the eye.

12. An adaptive optics method comprising:
measuring an aberration caused by a object, the aberration being measured on the basis of returning light that returns from the object;
performing aberration correction on the basis of a result of the aberration measured by the aberration measuring unit;
changing a diameter of light for irradiating the object on the basis of a result of the aberration measured by the aberration measuring unit after performing aberration correction; and
irradiating the object with the light whose diameter is changed.

13. The adaptive optics method according to claim 12, wherein the changing the diameter, reduces the diameter of the light in a case where an amount of the measured aberration after performing aberration correction satisfies a predetermined condition.

14. The adaptive optics method according to claim 13, wherein the changing the diameter, reduces the diameter of the light in a case where the amount of the aberration is larger than a predetermined value after a predetermined time interval from the start of the aberration correction.

15. The adaptive optics method according to claim 13,
wherein the object is a subject's eye, and
further comprising acquiring information based on a transmittance of an anterior segment of the subject's eye.

16. The adaptive optics method according to claim 15, wherein a portion having a low transmittance in the anterior segment of the subject's eye is irradiated with the light whose diameter is changed.

17. The adaptive optics method according to claim 12, further comprising:
a reporting unit that reports a result of the aberration measured by the aberration measuring unit.

18. The adaptive optics method according claim 12, wherein light uded to measure the aberration and light use to acquire an image of the object are emitted from the different light sources.

19. An imaging method, comprising:
the adaptive optics method according to claim 12; and
acquiring an image of the object on the basis of light that returns from the object irradiated with the light from the irradiation means.

20. The imaging method according to claim 19, further comprising:
separating light from into incident light, to be incident on the aberration correcting unit, and reference light,
wherein acquiring the image, acquires a tomographic image of the object on the basis of interference light resulting from interference between the light that returns from the object irradiated with the incident light and the reference light.

21. The imaging method according to claim 20, further comprising:
in a case where the measured aberration satisfies a predetermined condition, starting an operation of acquiring the tomographic image of the object after the diameter of the light form the light source is changed.

22. A non-transitory computer readable medium encoded with instructions to perform the adaptive optics method according to claim 12.

23. An adaptive optics apparatus comprising:
an measuring unit that measures an aberration of returning light that returns from an object;
an aberration correcting unit that performs aberration correction on the basis of a result of the aberration measured by the measuring unit;
a changing unit that changes a diameter of light for irradiating the object on the basis of the returning light measured by the aberration measuring unit after performing aberration correction; and
an irradiation unit that irradiates the object with the light whose diameter is changed by the changing unit.

24. An imaging apparatus, comprising:
the adaptive optics apparatus according to claim 23; and
an image acquiring unit that acquires an image of the object on the basis of light that returns from the object irradiated with the light from the irradiation unit.

25. The imaging apparatus according to claim 24, further comprising:
a separating unit that separates light from a light source into light to be incident on the aberration correcting unit and reference light,
wherein the image acquiring unit acquires a tomographic image of the object on the basis of interference light resulting from interference between the light that returns from the object irradiated with the light from the irradiation unit and the reference light.

26. The imaging apparatus according to claim 25, further comprising:
a starting unit that starts, in case where the aberration measured by the aberration measuring unit satisfies a predetermined condition, an operation of acquiring the tomographic image of the object after the diameter of the light from the light source is reduced by the changing unit.

27. The adaptive optics apparatus according to claim 23, wherein the object is an eye, and
wherein the aberration measuring unit and the aberration correcting unit are positioned optically conjugate with an anterior segment of the eye.

28. An imaging apparatus comprising:
an aberration measuring unit that measures an aberration of returning light that returns from an object irradiated with measurement light;
an aberration correcting unit that corrects at least one of an aberration of the measurement light and an aberration of the returning light on the basis of a measurement result obtained by the aberration measuring unit; and
a starting unit that starts an operation of acquiring a plurality of images at different positions in a depth direction of the object incase where an amount of the aberration measured by the aberration measuring unit is smaller than or equal to a predetermined value.

29. The imaging apparatus according to claim 28, further comprising:
a position changing unit that changes a focused position from a first position to a second position in accordance with a diameter of the measurement light, the second position being different from the first position in the depth direction,
wherein the plurality of images are acquired at the first position and the second position.

30. The imaging apparatus according to claim 28, wherein a single tomographic image is formed by combining the plurality of images.

31. The imaging apparatus according to claim 28,
wherein the object is an eye, and
wherein the aberration measuring unit and the aberration correcting unit are positioned optically conjugate with an anterior segment of the eye.

32. An adaptive optics method comprising:
measuring an aberration of returning light that returns from an object;
correcting aberration on the basis of a result of the measured aberration of the returning light;
changing a diameter of light for irradiating the object on the basis of the measured returning light after performing aberration correction; and
irradiating the object with the light whose diameter was changed.

33. The imaging method, comprising:
the adaptive optics method according to claim 32; and
acquiring an image of the object on the basis of light that returns from the object irradiated with light whose diameter was changed.

34. The imaging method according to claim 33, further comprising:
separating light into incident light and reference light, the incident light is the light for irradiating the object whose diameter was changed,
acquiring a tomographic image of the object on the basis of interference light resulting from interference between light that returns from the object irradiated with the incident light.

35. The imaging method according to claim 34, further comprising:
in a case where the measured aberration satisfies a predetermined condition, starting, acquiring the tomographic image of the object after the diameter of the light from the light source is reduced by the changing unit.

36. A non-transitory computer readable medium encoded with instructions to perform the imaging method according to claim 32.

37. An imaging method comprising:
measuring an aberration of returning light that returns from an object irradiated with measurement light;
correcting at least one of an aberration of the measurement light and an aberration of the returning light on the basis of the measured aberration of the returning light; and
starting acquiring a plurality of images at different positions in a depth direction of the object in a case where an amount of the aberration measured is smaller than or equal to a predetermined value.

38. The imaging method according to claim 37, further comprising:
changing a focused position from a first position to a second position in accordance with a diameter of the measurement light, the second position being different from the first position in the depth direction,
wherein the plurality of images are acquired at the first position and the second position.

39. The method according to claim 37, wherein a single tomographic image is formed by combining the plurality of images.

40. A non-transitory computer readable medium encoded with instructions to perform the imaging method according to claim 37.

41. An imaging apparatus comprising:
an aberration measuring unit that measures an aberration of returning light that returns from an object irradiated with measurement light;
an aberration correcting unit that corrects at least one of an aberration of the measurement light and an aberration of the returning light on the basis of a measurement result obtained by the aberration measuring unit;
a light-receiving unit that receives returning light that returns from the object with the corrected aberration;
a changing unit that changes a diameter of at least one of the measurement light and the returning light; and
a control unit that controls the changing unit on the basis of a light-receiving result obtained by the light-receiving unit.

42. The imaging apparatus according to claim 41, wherein the control unit is configured to control the changing unit such that the diameter is reduced in a case where intensity of the returning light received by the light-receiving unit is smaller than a threshold value.

43. The imaging apparatus according to claim 41, wherein the control unit is configured to change the changing unit such that the diameter is reduced in a case where a change in intensity in relation to a time of the returning light received by the light-receiving unit is smaller than a threshold value.

44. The imaging apparatus according to claim 41,
wherein the object is an eye, and
wherein the aberration measuring unit and the aberration correction unit are positioned optically conjugate with an anterior segment of the eye.

45. An imaging method comprising:
measuring an aberration of returning light that returns from an object irradiated with measurement light;
correcting at least one of an aberration of the measurement light and an aberration of the returning light on the basis of the measured aberration; and
controlling a changing unit on the basis of the returning light received by a light-receiving unit, the changing unit changing a diameter of at least one of the measurement light and the returning light, the light-receiving unit receiving returning light that returns from the object with the corrected aberration.

46. A non-transitory computer readable medium encoded with instructions to perform the imaging method according to claim 45.

47. The imaging method according to claim 45, wherein the controlling includes controlling the change such that the diameter is reduced in a case where intensity of the returning light received in the receiving is smaller than a threshold value.

48. The imaging method according to claim 45, wherein the controlling includes controlling the change such that the diameter is reduced in a case where a change in intensity in relation to a time of the returning light received in the receiving is smaller than a threshold value.

49. An imaging apparatus comprising:
an aberration measuring unit that measures an aberration of returning light that returns from an object irradiated with measurement light;
an aberration correcting unit that corrects at least one of an aberration of the measurement light and an aberration of the returning light on the basis of a measurement result obtained by the aberration measuring unit;
a light-receiving unit that receives returning light that returns from the object with the corrected aberration;
a position-changing unit configured to change a focal position of the measurement light from a first position to a second position different from the first position in a depth direction; and
a control unit configured to control the position-changing unit based on a light-receiving result obtained by the light-receiving unit such that a plurality of images of the object is acquired at the first position and second position 50. The imaging apparatus according to claim 49, wherein the control unit is configured to control the position-changing unit such that the plurality of images is acquired in case where intensity of the returning light received by the light-receiving unit is equal to or larger than a threshold value.

51. The imaging apparatus according to claim 49, wherein the control unit is configured to control the position-changing unit such that the plurality of images is acquired in a case where a change in intensity in relation to a time to the returning light received by the light-receiving unit is smaller than a threshold value.

52. The imaging apparatus according to claim 49, further comprising:
a forming unit configured to form one tomographic image by combining the plurality of acquired images.

53. The imaging apparatus according to claim 49,
wherein the object is an eye, and
wherein the aberration measuring unit and the aberration correcting unit are positioned optically conjugate with an anterior segment of the eye.

54. An imaging method comprising:
measurement an aberration of returning light that returns from object irradiated with measurement light;
correcting at least one of an aberration of the measurement light and an aberration of the returning light on the basis of the measured aberration; and
controlling a position-changing unit that changes a focal position of the measurement light from a first position to a second position different from the first position in a depth direction based on a light-receiving result obtained by a light-receiving unit that receives the returning light that returns from the object with the corrected aberration such that a plurality of images of the object is acquired at the first position and the second position.

55. A non-transitory computer readable medium encoded with instructions to perform the imaging method according to claim 54.

56. The imaging method according to claim 54, wherein the controlling includes controlling the position-changing unit such that the plurality of images is acquired in a case where intensity of the returning light received by the light-receiving unit is equal to or larger than a threshold value.

57. The imaging method according to claim 54, wherein the controlling includes controlling the position-changing unit such that the plurality of images is acquired in a case where a change in intensity in relation to a time of the returning light received by the light-receiving unit is smaller than a threshold value.

58. The imaging method according to claim 54, further comprising:
   forming one tomographic image by combining the plurality of acquired images.

* * * * *